United States Patent [19]
Lillbacka

[11] Patent Number: 6,079,424
[45] Date of Patent: Jun. 27, 2000

[54] METHOD AND ARRANGEMENT FOR TENSIONING DENTAL FLOSS, AND A DEVICE FOR CLEANING TEETH

[75] Inventor: Antti Lillbacka, Ylihärmä, Finland

[73] Assignee: Xylifloss Oy Ltd, Tampere, Finland

[21] Appl. No.: 09/202,537

[22] PCT Filed: Jun. 16, 1997

[86] PCT No.: PCT/FI97/00382

§ 371 Date: Dec. 16, 1998

§ 102(e) Date: Dec. 16, 1998

[87] PCT Pub. No.: WO97/48349

PCT Pub. Date: Dec. 24, 1997

[30] Foreign Application Priority Data

Jun. 17, 1996 [FI] Finland ................................. 962515

[51] Int. Cl.[7] ............................................. A61C 15/00
[52] U.S. Cl. ............................................. 132/326; 132/327
[58] Field of Search ............................. 132/323, 324, 132/325, 326, 327; 433/141

[56] References Cited

U.S. PATENT DOCUMENTS

| | | | |
|---|---|---|---|
| 2,182,525 | 12/1939 | May | 132/326 |
| 2,460,591 | 2/1949 | Luzar | 132/326 |
| 2,724,390 | 11/1955 | Sokoloski | 132/326 |
| 3,327,719 | 6/1967 | Ford | 132/326 |
| 3,376,876 | 4/1968 | Wicklund | 132/324 |
| 3,592,203 | 7/1971 | Johnson | 132/323 |
| 3,814,114 | 6/1974 | Roberts | 132/325 |
| 3,871,393 | 3/1975 | Wharton | 132/326 |
| 3,903,907 | 9/1975 | Knaus | 132/326 |
| 4,495,956 | 1/1985 | Fourie | 132/326 |
| 4,637,412 | 1/1987 | Martinez | 132/323 |
| 4,738,271 | 4/1988 | Bianco | 132/323 |
| 4,936,326 | 6/1990 | Eckroat | 132/326 |
| 5,197,498 | 3/1993 | Stewart | 132/325 |
| 5,301,699 | 4/1994 | Craft | 132/325 |

FOREIGN PATENT DOCUMENTS

| | | |
|---|---|---|
| 82806 | 1/1991 | Finland . |
| 2040686A | 9/1980 | United Kingdom . |
| 8809646 | 12/1988 | WIPO . |

*Primary Examiner*—Todd E. Manahan
*Attorney, Agent, or Firm*—Birch, Stewart, Kolasch & Birch, LLP

[57] ABSTRACT

A device and method for holding and tensioning dental floss. The device has a tensioning element which is rotatable within the device body, with a tensioning passage and a guide passage located at opposite ends of the tensioning element. The tensioning passage and the guide passage are offset by an angle which allows the floss to be secured when the tensioning element is rotated, without introducing excessive tension in the strand.

25 Claims, 4 Drawing Sheets

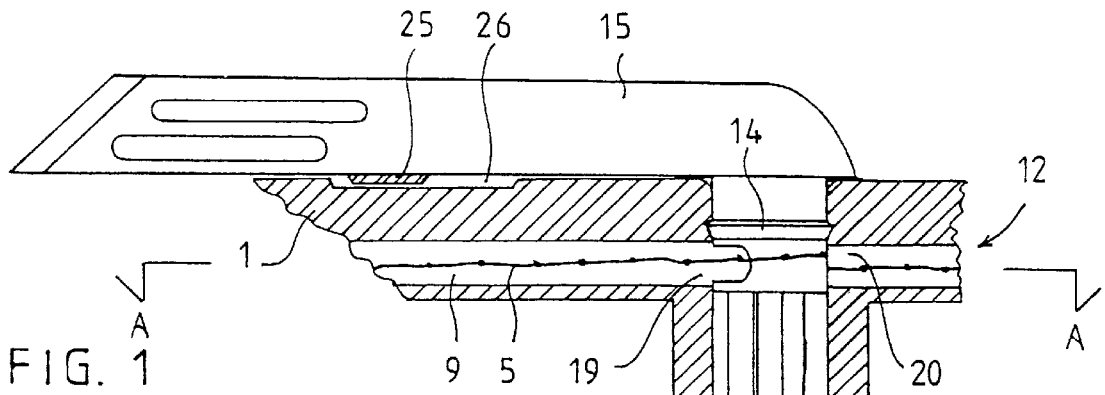
FIG. 1
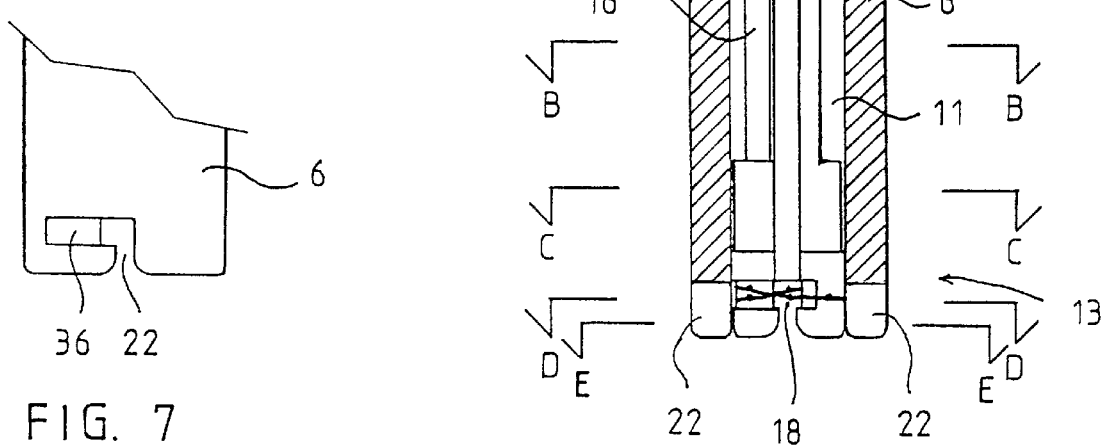
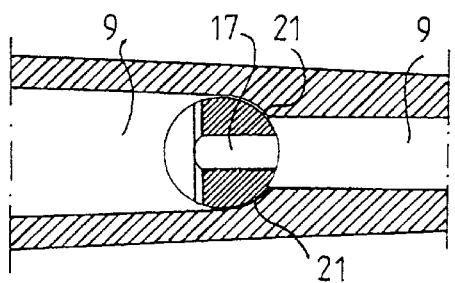
FIG. 7
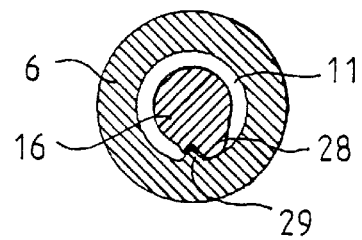
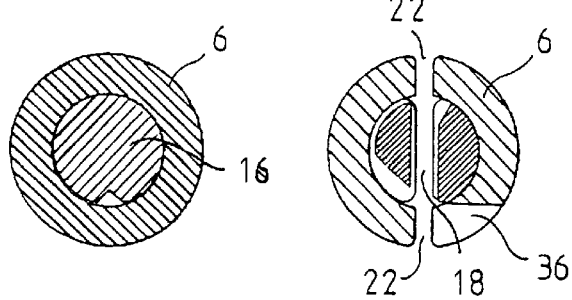
FIG. 2
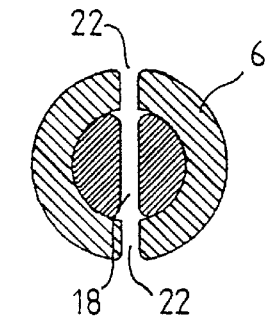
FIG. 3
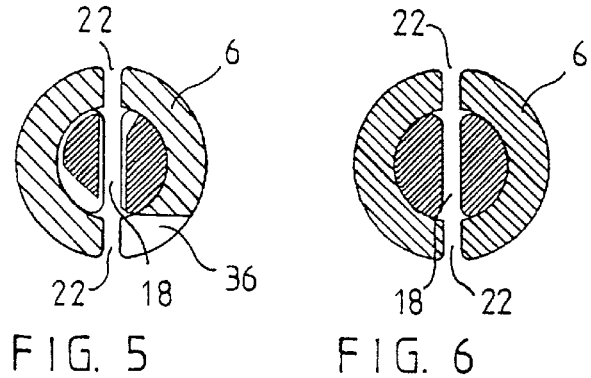
FIG. 4    FIG. 5    FIG. 6

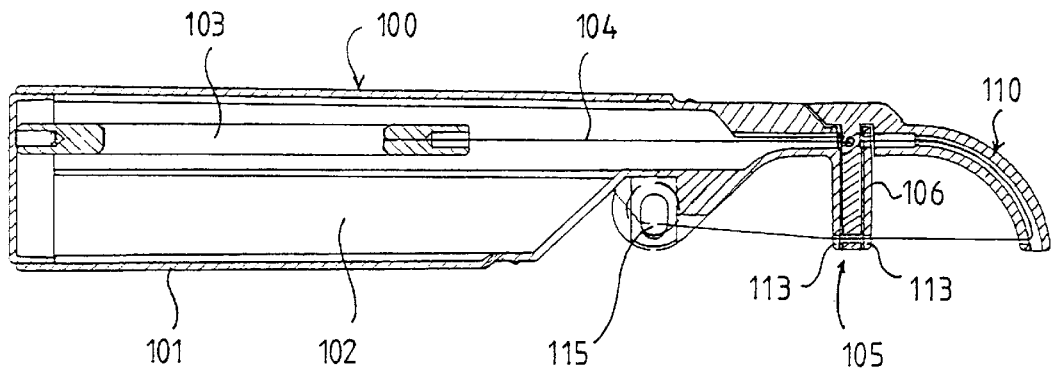
FIG. 19
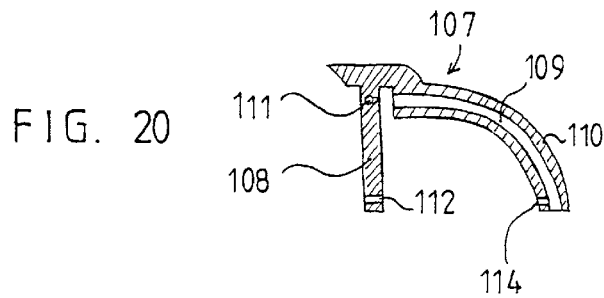
FIG. 20
FIG. 21
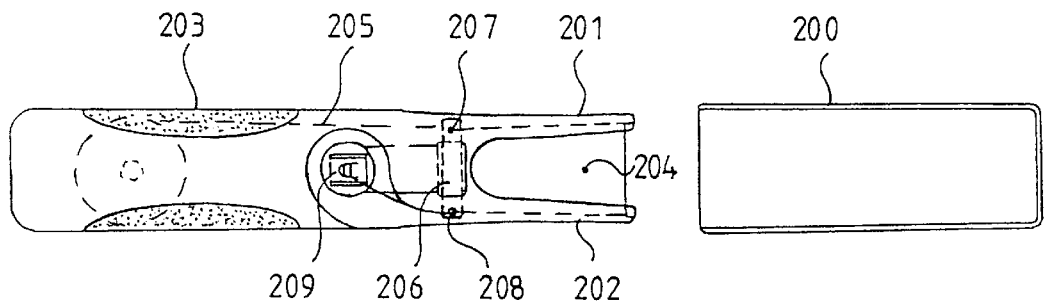
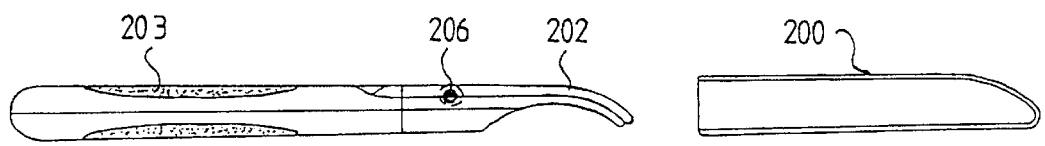
FIG. 22

6,079,424

METHOD AND ARRANGEMENT FOR TENSIONING DENTAL FLOSS, AND A DEVICE FOR CLEANING TEETH

This application is the national phase under 35 U.S.C. §371 of prior PCT International Application No. PCT/FI97/00382 which has an International filing date of Jun. 16, 1997 which designated the United States of America.

The present invention relates to a method as claimed in the preamble of claim 1.

The invention further relates to a tensioning means according to such a method, set forth in the preamble of claim 4.

The method and tensioning means of the invention are applied in dental floss holding devices according to the preambles of claims 11 and 15.

An important part of taking care of dental hygiene is to clean the spaces between teeth. Such personal hygiene may be taken care of with toothpicks and, moreover, with dental floss. When employing dental floss, the user has available several options. The dental floss may be held and guided by fingers, but it may also be secured to various kinds of holders which seek to facilitate the use of the dental floss. Various types of such holders exist; devices are known in which a piece of dental floss cut from a supply thereof is inserted to dental floss holders. Most commonly, though, the dental floss is secured to dental floss holders of a holding device so that the dental floss is wound around mounting slots in which e.g. ridges have been provided to keep the dental floss tight between the floss holders. Such devices are disclosed e.g. in U.S. Pat. Nos. 3,376,876 and 3,871,393.

There are also devices, such as those disclosed in the patent publications FI 82 806, GB 2 040 686, U.S. Pat. No. 2,274,390 or U.S. Pat. No. 5,197,498, in which the dental floss is incorporated in the device itself. The floss is guided to the floss holders of the device and is locked between the holders with different kinds of locking mechanisms provided in the device.

It is especially noteworthy to mention the device according to U.S. Pat. No. 3,814,114, into whose handle has been arranged a means that tightens the dental floss. In such a device, the dental floss is arranged to squeeze between the outer shell of the tightening device and the inner wall of the cavity-like space which receives the means.

The known devices share the drawback that when cleaning the spaces between teeth, the dental floss will none the less move in the device, and consequently loosen between its holders. If the floss loosens, the cleaning of teeth becomes difficult and the floss will have to be tightened over and over again. On the other hand, the floss is sometimes in a number of such devices unintentionally tightened too much, which results in that the cleaning of the spaces between teeth becomes truly unpleasant. If the floss is too tight, the cleaning will become impossible as the floss does not yield and is consequently unable to follow the tooth surface being cleaned.

The prior art devices further have the drawback that the elements guiding the floss will easily become affected by saliva, washing water or other impurities. This, in turn, causes the dental floss stored within the device to get dirty.

Additionally, the placement of dental floss in holders in many of the known devices is difficult. As the device and the floss holders therein must be small to fit in the mouth, it is difficult to discern where in the device and how to fit and secure the floss.

It is common practice with the known devices to provide them with various kinds of gripping means which in use cause the dental floss to fray, thus quickly spoiling it.

SUMMARY OF THE INVENTION

It is an object of the present invention to remove the prior art drawbacks and to provide a new type of solution by means of which it is ensured that the dental floss is kept tight and undamaged between the dental floss holders. Further, it is an aim of the invention to obtain a device which is hygienic and easy to use.

This object can be obtained by a tensioning element which is rotatable within the device body, with a tensioning passage and a guide passage located at opposite ends of the tensioning element. The tensioning passage and the guide passage are offset by an angle which allows the floss to be secured when the tensioning element is rotated, without introducing excessive tension in the floss strand. The angular offset between the guide passage and the tensioning passage allows one lock element to begin tensioning the floss while the other lock allows floss to move freely through the tensioning passage, thus preventing excessive tension in the floss.

By winding a predetermined length of dental floss around the tensioning means, the dental floss will always tighten to a correct tension, thus allowing comfortable use. The tensioning of the dental floss is according to the inventive method ensured by guiding the floss to the tensioning means from the so-called free ends of the floss, that is, from the axle storing the floss and from the end of the floss outside the device. Consequently, the amount of floss that will wound from between the floss holders to around the tensioning means is reduced, whereby the floss will not be allowed to tighten to a disadvantageous degree.

The tensioning means according to the invention for tensioning dental floss involves shaping the guiding and/or tensioning passages with various kinds of guiding means to restrict the movement of the floss in the direction of the tensioning means, and to adjust its tension.

More specifically, the device of the invention advantageously comprises a plastic body with a handle within which dental floss has been arranged. The floss is guided to floss holders, separate from the handle and protruding from the device in its front part, between which the floss is tensioned. It is easy to arrange a cutting means at the side of the device, by means of which floss that has been used for cleaning may be cut and removed from the device.

In the device of the invention, the floss holders are located at the hypothetical extension of the handle so that they are clearly apart from the handle section of the device. In the operative position, it is advantageous for the floss holders to be located on the same cutting plane, which is also the symmetry plane of the device. Due to the thin finger-like floss holders, the device is easy to use for cleaning all the spaces between teeth, both in the front part of the mouth and in the usually hard to reach back part.

Contrary to the prior art devices, the dental floss tensioning means in the device according to the invention is arranged in a joint passage at the handle side of the floss holder, in which it is arranged to rotate about its longitudinal axis, thus tensioning and locking the dental floss in its operative position. With the present device, exactly the correct tension is achieved for the floss, which may due to the structure of the locking mechanism be maintained over the entire period of use.

The inventive dental floss holder allows a separate, rotary tip part be arranged in the joint passage. Such a tip part comprises a tensioning means and an outer floss holder rigidly connected thereto, and a floss passage extending from the tensioning means to the tip of the outer floss holder, whereby it is possible to turn the outer floss holder with respect to the longitudinal axis of the device.

The outer floss holder of the device according to the invention may also be arranged to turn by arranging an outer floss holder provided with a barrel around the inner floss holder comprised in the tensioning means. In such a case, the floss holder farthest out comprises a floss passage of the type described above for guiding the dental floss to a cleaning gap of the device.

By arranging the tensioning means into the body substantially transversely in relation to the longitudinal axis of the body, the floss holders of the device protrude fork-like from the body, and the dental floss is wound around the tensioning means by a movement of the tensioning means in relation to the body, thus locking the floss into place.

In the devices according to the invention, the mounting and tensioning of the floss is carried out by arranging a space, a joint passage, in the floss holder at the handle side of the devices or into the body of devices, into which the floss tensioning means, for example a bar-like element such as a yoke, may be installed. This yoke is provided with guiding means such as holes through which the dental floss from the handle of the device is arranged to travel. By changing the position of the guiding means in relation to the device body, the dental floss may be freed to move on the floss holders. By arranging the yoke in a locked position, that is further deviating the yoke in the floss holder space in relation to the device body, such as by turning it, the floss may be wound around the tensioning means and it may thus be tensioned and locked securely in the operative position between the tips of the floss holder. By changing the shape of at least one guiding element of the yoke, as in providing it with so-called grip notches, the dental floss may be prevented from tensioning too much between the floss holders. In this manner, exactly the correct tension will be obtained for the floss, so that it is not unpleasant to use and does not harm the gum line when in use.

By the method and tensioning means according to the invention, the dental floss is subjected to an advantageous controlled loosening at its tensioning stage. The controlled loosening of the floss to the correct tension is of utmost importance, as this facilitates cleaning the round surfaces of teeth and prevents the floss from fraying.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 shows a preferred embodiment of a tensioning means mounted in a floss holder of the device, with the floss holder and the body cut open, FIG. 2 shows a horizontal view of the top lock in the tensioning means without dental floss, cut open at point A—A of FIG. 1, FIG. 3 shows a horizontal view of an embodiment for a mechanism preventing the tensioning means from turning, without dental floss at point B—B of FIG. 1, FIG. 4 shows a horizontal view of the tensioning means without dental floss at point C—C of FIG. 1, FIG. 5 shows a horizontal view of the bottom lock in the tensioning means without dental floss, cut open at point D—D of FIG. 1, FIG. 6 shows a horizontal view of an embodiment of the securing element of the tensioning means at point E—E of FIG. 1 without dental floss, FIG. 7 illustrates a structural detail of the floss holder tip of the floss holder receiving the tensioning means, as seen from the side, FIG. 19 shows a lengthwise section of the teeth cleaning device according to the invention, having a rotary tip part, FIG. 20 is a detailed view of the tip part of the device according to FIG. 19, FIG. 21 shows a top view of the teeth cleaning device according to the invention, having floss holders in the direction of the longitudinal axis of the body, and FIG. 22 shows a side view of the teeth cleaning device according to FIG. 21.

DETAILED DESCRIPTION OF THE PREFERRED EMBODIMENTS

Figure 8:
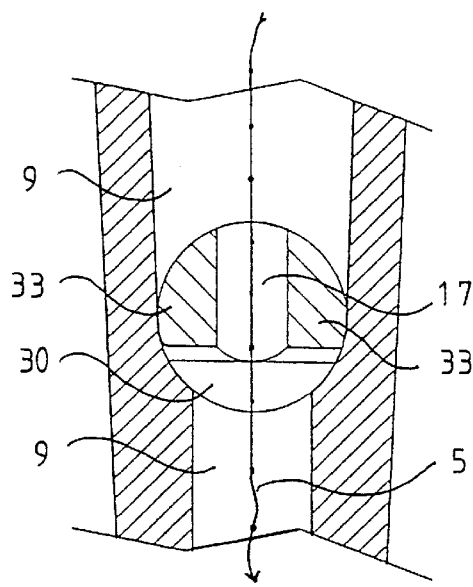
FIG. 8 shows a tensioning passage of a tensioning means according to an embodiment, with dental floss, ready for operation.
Figure 9:
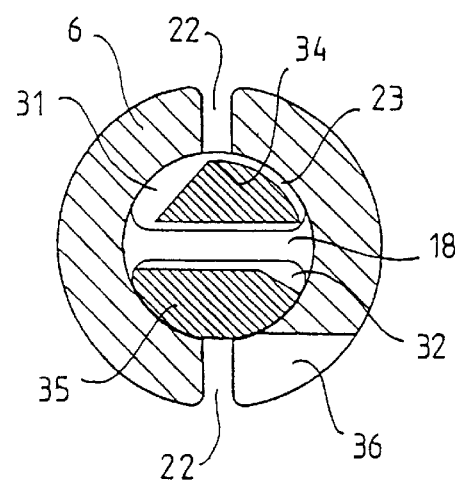
FIG. 9 shows the guide passage of the tensioning means in a situation according to FIG. 8.

The method according to the present invention for tensioning dental floss will be described with reference to a preferred embodiment of the teeth cleaning device, illustrated in FIGS. 14–18. The device comprises a body 1, advantageously made from plastic by moulding. The body comprises a handle 2, into which has been formed a cavity 3. In this cavity, an axle 4 has been arranged around which dental floss 5 is reeled to be used for cleaning the spaces between teeth. The body further comprises inner and outer floss holders 6 and 7 that are apart from the handle and hollow. To guide the dental floss to the operative region, the device comprises a floss passage 9 extending from the cavity 3 via the inner floss holder 6 at the handle side to the tip 8 of the outer floss holder 7.

The floss holders are advantageously located at the hypothetical extension of the handle 2 so that they are clearly apart from the handle part of the device. In the preferred embodiment of the device according to FIGS. 14 and 15, the floss holders are advantageously placed, in their operative position, at the same shear plane with the body. The floss holders are thin and finger-like, whereby a cleaning gap 10 is formed between them. The dental floss is arranged in the cleaning gap 10. When placing between teeth the portion of the dental floss that is between the floss holders, the spaces between teeth may be cleaned by moving the device gently back and forth.

The device comprises a joint passage 11 into which has been arranged a tensioning means 16 according to FIGS. 1–6, provided with so-called top and bottom locks 12 and 13, a securing element 14 and a turning element 15, such as an arm. Said top and bottom locks comprise structures receiving the floss and restricting its movement. Such structures are represented by holes, shown in the figures as a tensioning passage 17 and a guide passage 18, arranged to pass substantially through the tensioning means 16 and being perpendicular to its longitudinal axis. The wall in the floss holder 6 at the inner handle 2 side comprises gaps 19 and 20 for feeding the floss through, whereby they are located at places corresponding to the beginning and end of the tensioning passage 17 of the tensioning means 16 when said passage is positioned parallel to the longitudinal axis of the device. The floss passage 9 extending to the tip 8 of the outer floss holder 7 is arranged to narrow at the top lock 12 so that at floss holder gap 20 at the tip side of the device, cheek surfaces 21 immediately in connection with the top lock have been formed in the floss passage together with the joint passage 11. The guide passage 19 at the tip side of the tensioning means may be formed by a notched slot, a hole formed at the tip of the tensioning means, or a notch which is wider at the bottom, into which the dental floss is placed. In connection with the guide passage, the ends of the floss holders also comprise receiving passages or means 22, such as slots or holes, for receiving floss 5 and guiding it to the guide passage.

In the method according to the invention, dental floss is tensioned between floss holders provided in the dental floss holding device so that the floss is first guided along the floss passage 9 to the joint passage 11 via a tensioning passage 17 of the tensioning means 16 arranged in the joint passage 11 (shown in FIG. 8) further along the floss passage to the tip 8 of the outer floss holder 7. From thereon, the floss is fed over the cleaning gap 10 and further through a guide passage 18 provided at the tip of the floss holder 6 at the handle side (shown in FIG. 11). Following this, the floss is tensioned and locked into the device by a rotational movement of the tensioning means 16, as shown by FIGS. 10–13. This means that the tensioning means is rotated about its axis that passes through the tensioning passage 17 and the guide passage 18, so that the dental floss is wound at the tensioning means. As the dental floss 5 is placed on the shell of the tensioning means, between the surfaces of the tensioning, and guide passages and other floss that is gathered thereon, friction will be obtained that prevents the floss from moving.

By releasing the floss for a relative movement taking place in connection with the tensioning means 16, it is possible to prevent too much dental floss from winding around the tensioning means during the rotary movement applied to the tensioning means.

In the preferred embodiment of the invention, the tensioning passage 17 in the top lock 12 of the tensioning means 16 located in the joint passage 11 of the floss holder 6 at the handle side, and the guide passage 18 in the bottom lock 13 are arranged to pass through the securing means in different directions, advantageously at an angle of approximately 90° to one another. When threading dental floss to such a device, the tensioning passage must be turned parallel to the longitudinal axis of the device, whereby the guide passage will be arranged in the device transversely. When the floss threading is continued, the guide passage has to be rotated to be parallel to the longitudinal axis of the device so that the floss could be arranged in it. As a consequence, however, the tensioning passage 17 turns to a transverse direction in relation to the longitudinal axis of the device, causing a greater friction on the dental floss. Hence, the tensioning passage in a transverse position hinders the movements of the floss, keeping it at the correct tension between floss holders 6 and 7 of the device.

Arranging the floss in this manner to an advantageous tension consequently facilitates mounting it to the guide passage 18.

Figure 10:
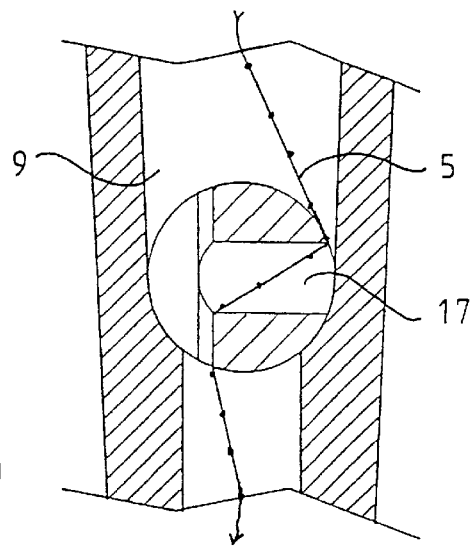
FIG. 10 shows a tensioning passage of a tensioning means according to an embodiment in a shifting position, i.e. the dental floss released.

By rotating the tensioning means in the way described above to a threading position according to the bottom lock (shown in FIG. 11), the top lock simultaneously pulls dental floss from the axle (shown in FIG. 10). When the dental floss holder according to the invention is taken in use, the tensioning means is rotated at least 180°, advantageously 270° (shown in FIGS. 12 and 13) to achieve an adequate friction surface and an advantageous overlap of the dental floss. When the top lock 12 is rotated into the locking position, the dental floss gathered at the tensioning passage 17 during the threading or mounting stage of the guide passage 18 will be released first. This means that the tensioning passage 17 may be rotated substantially 180° before new floss begins to gather thereto either from the region between the tensioning passage 17 and the floss holder 6 at the handle side, or from the axle 4. As a consequence, the top lock has no influence at all on the tension of the floss during the first two thirds of the rotational movement of the tensioning means. The passing of the floss from the axle 4 to the top lock 12 is substantially prevented only when the outer shell of the tensioning means 16 meets both of the so-called cheek surfaces 21 located in conjunction with the top lock of the joint passage 11. During the last one third of the rotational movement of the tensioning means, the tensioning means partly slides on the floss that is between the outer shell of the tensioning means and the joint passage wall, and partly the floss is pulled about the tensioning means from between the floss holders and/or the axle.

In the bottom lock 13, the tensioning means 16 slides on the outer surface of the floss 5 as the tensioning means is being rotated to the locking position. Such sliding is produced by a braking force exerted on the floss by the top lock, whereby the transfer and the consequent winding of the floss about the bottom lock is substantially prevented. As a matter of fact, dental floss is during the rotational movement transferred to the bottom lock from the free end of the floss, that is, the end which is external to the cleaning gap 10. There is thus arranged a floss groove 23 to receive the floss that is left between the outer shell of the tensioning means and the inner surface of the joint passage. Thus, the floss groove prevents the friction coefficient between the dental floss and the bottom lock from becoming too high, and helps the bottom lock slide on the floss that has set against the inner surface of the joint passage. During substantially the last one fourth of the locking movement, the dental floss is arranged twofold at location 24 in the bottom lock area, producing together with the friction coefficient between the bottom lock and the floss, an adequate traction force to the floss so as to pull floss from between the floss holders to around the bottom lock, thus tensioning the floss in the device to its correct tension.

Figure 11:
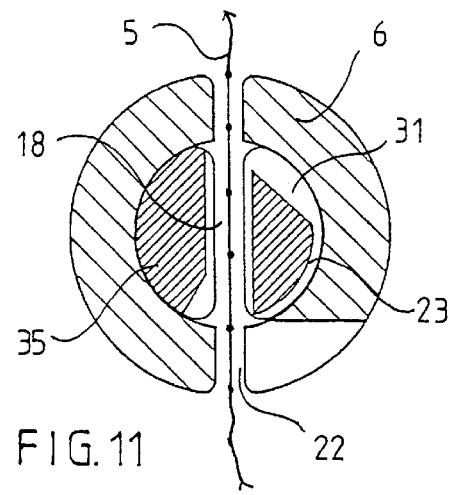
FIG. 11 shows a guide passage of the tensioning means in a situation according to FIG. 10, this situation being also the inserting phase of the dental floss into the guide passage.
Figure 12:
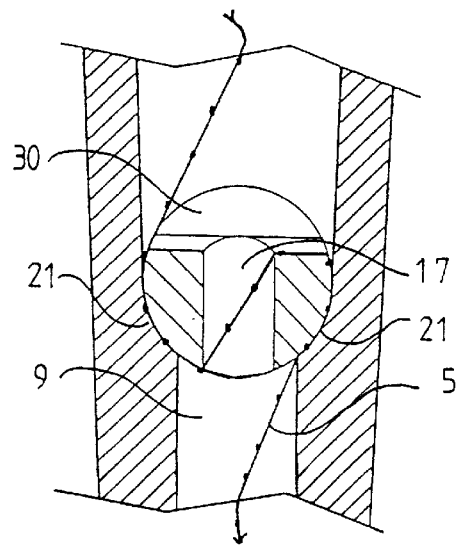
FIG. 12 shows the guide passage of the tensioning means according to an embodiment at the dental floss locking position, i.e. with the tensioning means having rotated 270° from the shifting position of FIG. 10.
Figure 13:
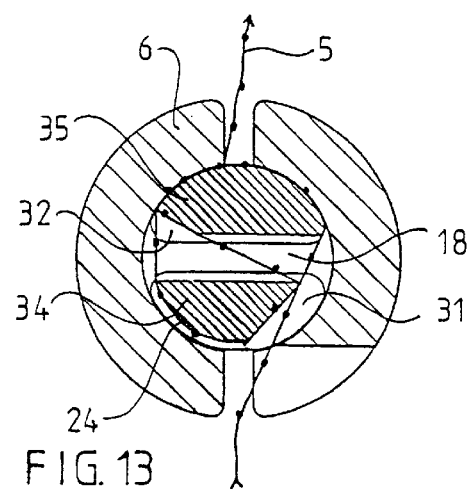
FIG. 13 shows the guide passage of the tensioning means in a situation according to FIG. 12.
Figure 14:
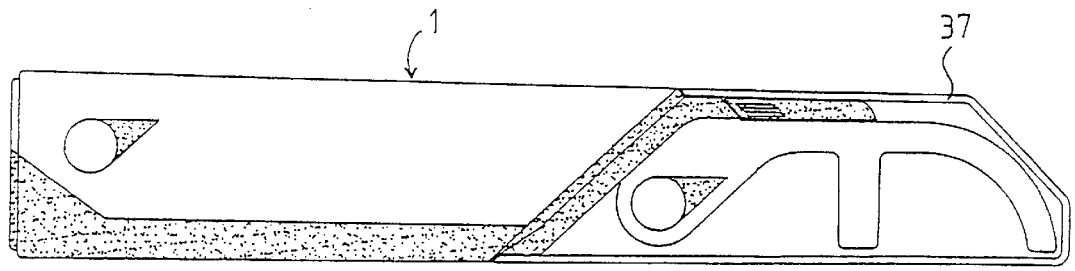
FIG. 14 shows a preferred embodiment of the device according to the invention.

An advantageous arrangement for tensioning and locking dental floss in a dental floss holding device is shown by FIGS. 1–6. According to the arrangement, the securing and tensioning of the floss 5 is implemented so that the floss is guided via the floss passage 9 to the tensioning means 16 at the joint passage 11 of the device. The tensioning means comprises top and bottom locks 12 and 13 according to FIG. 1, which contain the tensioning passage 17 and the guide passage 18 which are arranged to pass through the tensioning means in different directions and which receive the dental floss. In the preferred embodiment of the figure, the passages advantageously form an angle of approximately 90° with respect to one another. The dental floss in such a case is further applied through the tensioning passage 17 by arranging the tensioning passage comprised by the tensioning means to a position parallel to the longitudinal axis of the device (FIG. 8) by rotating the turning arm 15 of the device. From this position, the floss is further guided to the floss passage 9 and the outer floss holder 7. From the tip 8 of the floss holder, the floss is fed to between the floss holders in the cleaning gap 10. While in the region of the floss holder 6 at the handle side, the floss is arranged to the guide passage 18 in the bottom lock 13 of the tensioning means 16 by arranging, in turn, the guide passage to a position parallel to the longitudinal axis of the device by rotating the turning arm 15 in the tensioning means (FIG. 11). Finally, the dental floss is tightened into the cleaning gap 10 of the device by rotating the turning arm 15 to be parallel to the body 1 of the device so that a locking element 25 in the turning arm will be guided to a locking groove 26 in the body. After this, the surplus end of floss is removed by cutting it with a cutting element 27 provided in the device.

The dental floss 5 is thus mounted and tensioned between the floss holders 6, 7 by rotating the tensioning means 16 about its longitudinal axis. In the embodiment according to FIGS. 1–18, this rotational movement is substantially 270°, or three fourths of a turn. Consequently, both ends of the dental floss travelling via the tensioning means is subjected to, towards the end part of the rotational movement, a traction force as the floss is wound about the tensioning means. The portion of the floss that extends from the tensioning passage 17 of the tensioning means via the outer floss holder 7 to the guide passage 18 will become shorter as the floss is tensioned about the tensioning means, thus tensioning the floss between the tips of the floss holders 6, 7.

In the device according to the invention, the floss 5 is securely locked into place when it is tensioned. The locking of the floss is achieved on the one hand with the friction between the wall surfaces of the top and bottom locks 12 and 13, and on the other hand, with the pressing created on the floss by the tensioning means 16 outer shell and the surrounding inner wall in the joint passage 11 of the floss holder 6. The pressing taking place at the cheek surfaces 21 locally creates a stronger friction for the floss as the floss is clamped between the cheek surfaces.

If the guide passage 18 is again rotated to be parallel with the longitudinal axis of the device, the end of the floss may be gripped and a new, unused portion of floss be pulled between the floss holder tips and secured to the operative position.

The rotational movement of the tensioning means 16 may be restricted by arranging, according to FIG. 3, a projecting part 28 thereto which upon touching a ridge 29 formed in the wall of the joint passage 11 prevents the movement of the turning arm 15, thus limiting the rotation of the tensioning means.

In a preferred embodiment of the invention, the end of the top and bottom locks 12 and 13 of the tensioning means is arranged to be larger than the rest of the passage by arranging the passage in the shape of a bevel or by arranging indentations, so-called grip notches 30, 31, 32, in connection with them. The movements of the dental floss are further influenced by arranging in connection with the guiding element at least one floss groove 23 (cf. FIGS. 8–13). Due to these notches, the floss does not have to travel on the outer surface of the tensioning means 16, but it travels part of its journey linearly via a shorter route to a hole 19 and 20 in the wall of the joint passage 11. Consequently, there will be less dental floss winding around the tensioning means while the grip notches 30–32 and the floss groove 23 partly allow the movements of the floss in the top and bottom locks 12 and 13 during the rotational movement of the tensioning means. Via the grip notches and the floss groove, dental floss will travel to an area where the floss will be tensioned, that is, to an area bordered by the tensioning passage 17, the floss passage 9 of the outer floss holder 7, the cleaning gap 10 between the floss holders, and the guide passage 18. Thus, floss 5 is transferred from the axle 4 to the tensioning area of the floss until the shell of the tensioning means 16 meets the cheek surfaces 21 of the joint passage 11. In addition, dental floss is transferred from its free end from outside of the guide passage along the floss groove 23 advantageously until the dental floss in the bottom lock 13 is wound at the end of the locking motion twofold on the surface of the tensioning means at the position 24 on the shell of the tensioning means. From the user's point of view, it is in this manner possible to achieve a pleasant tension for the floss between the floss holders. The floss groove 23 also prevents the floss from squeezing too much between the joint passage 11 and the shell of the tensioning means 16, thus preventing the floss from getting stuck in the bottom lock as new floss is being shifted to between the loss holders.

A preferred embodiment for the grip notches is shown in FIGS. 1–13. In this embodiment, a grip notch 30 is formed in the tensioning passage 17 in connection with the top lock 12, so that while the passage is in a locking position (FIG. 12), the notch consists of a segment removed from the tensioning passage 17 end opposite to the cheek surfaces 21 of the joint passage 11, whereby a part substantially of equal size has been removed from body segments 33 of the tensioning means, which are located at both sides of the tensioning passage. In this manner, the floss that is tensioned to its operational position will independent of the grip notch be clamped between the walls of the tensioning means and the joint passage, creating a larger friction coefficient. The notch 30 does, however, allow the floss to slide through the tensioning passage 17 for the most part of the rotational movement of the tensioning means.

Furthermore in connection with the bottom lock 13, grip notches 31 and 32 have been arranged so that when the tensioning means 16 is in the locking position (FIG. 13), the first grip notch 31 is formed to the body segment 34 at the side of the floss holder 7 of the tensioning means and constituted by the guide passage 18, from a notch arranged at the other end of the passage and substantially having a form of a sector. In addition, a second grip notch 32 substantially having the form of a segment is arranged at a body segment 35 which is formed by the guide passage 18 and which is opposite to the outer floss holder of the tensioning means, to the end opposite to the previous first grip notch 31 of the guide passage. Further, in connection with this notch, a floss groove 23 is arranged which extends from the second grip notch 32 along the outer surface of the body segment 34 to the end of the guide passage 18, located at the first grip notch 31. In this manner, the floss 5 tensioned at the operative position is squeezed between the walls of the tensioning means and the joint passage, creating a higher friction coefficient. At the same time, the floss passage prevents the floss from sticking too tightly to the wall of the joint passage.

Advantageously, at the tip of the floss holder surrounding the tensioning means, a guiding slot 36 is arranged in connection with a receiving element 22 at the side of the outer floss holder 7, said guiding slot being employed for preventing the floss from detaching during use.

An advantageous embodiment of the floss holding device is illustrated by FIGS. 14–18. The tensioning means 16 provided with tensioning and guide passages 17 is arranged in a floss holder 6 at the handle side, or the first floss holder. The opposite walls of the floss holder 6 comprise holes 19 and 20 for feeding through floss 5, whereby the holes are located parallel to the longitudinal axis of the device body, at the start and end points of the tensioning passage 17 in the tensioning means 16. The tensioning means 16 is installed in the first floss holder 6 by pushing a tensioning element into a joint passage 11 that is located in the floss holder in the direction of the longitudinal axis. The tensioning passage is locked into place by means such as flexible claws provided at its ends, or so that a flange 14 in the tensioning means is positioned in an ear in the inner wall of the joint passage.

Figure 15:
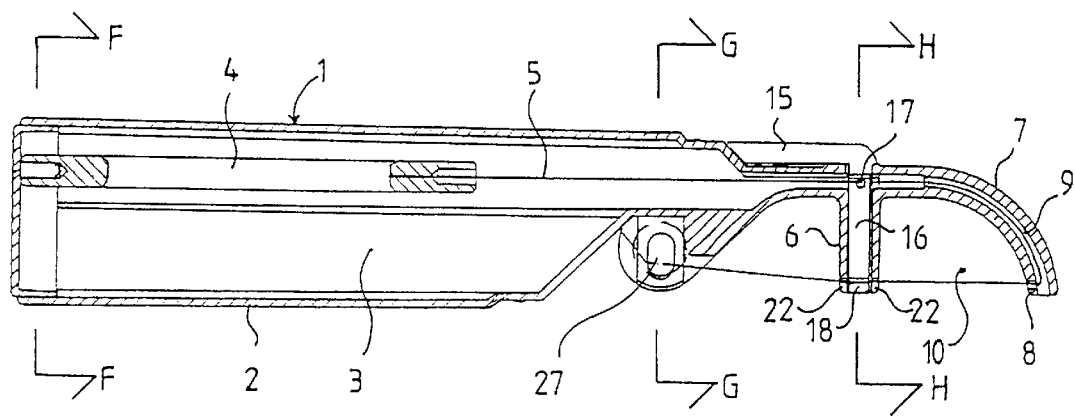
FIG. 15 shows a lengthwise section of the device according to FIG. 14.
Figure 16:
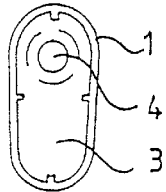
FIG. 16 shows a cross section of the point F—F in FIG. 15.
Figures 17, 18:
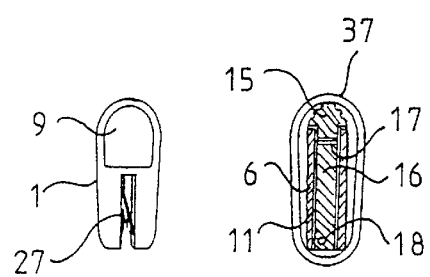
FIG. 17 shows a cross section of the point G—G in FIG. 15.
FIG. 18 shows a cross section of the point H—H in FIG. 15.

The dental floss 5 is in the device according to the invention guided, as shown by FIG. 15, so that the floss wound on the axle 4 in the cavity 3 of the handle 2 is guided from the axle to the first floss holder 6 which comprises the tensioning means 16 provided with the tensioning and guide passages 17 and 18. The floss 5 is applied through the tensioning passage at the base side of the tensioning means; it is guided further along the floss passage 9 in the outer, the second, floss holder 7, exiting at the open end in the tip 8 of the floss holder. Further, the floss 5 is taken back to the first floss holder 6 and consequently attached to the guide passage 18 at the end of the tensioning means 16. As to its longest portion, the floss is therefore protected inside the device, in addition to which it may during transfer be protected by a cover part 37 provided in the device.

FIGS. 19 and 20 illustrate another preferred embodiment of the dental floss holder according to the invention. The device set forth comprises a body 100 with a handle 101 into which has been formed a cavity 102. This cavity is provided with an axle 103 onto which dental floss 104 has been wound. The body further comprises, separate from the handle, a first floss holder 105 into which a joint passage 106 has been formed. Into the joint passage of the floss holder, a tip part 107 has been arranged which comprises a tensioning means 108 and an outer or second floss holder 110 rigidly secured thereto and provided with a floss passage 109. The tensioning means contains tensioning and guide passages 111 and 112. The opposite walls in the first floss holder 105 comprised by the body have holes for leading through the dental floss 104, whereby they are located at places corresponding to the start and end points of a tensioning passage 111 in the tensioning means 108 of the tip part 107 when it is in a parallel direction with the longitudinal axis of the device. The tip of the first floss holder 105, receiving the tensioning means 108, also comprises receiving elements 113 for receiving the dental floss 104 and for arranging it into the guide passage 112.

The tip part 107 is fit in the first floss holder 105 by pushing the tensioning means 108 into the joint passage 106 comprised, parallel to the longitudinal axis of the device, by the floss holder. The tensioning means is locked into place by means of such as flexible claws provided at its ends, or so that a flange in the tensioning means is positioned in an ear (not shown) in the inner wall of the joint passage.

The dental floss 104 is in a device according to this embodiment guided as shown by FIG. 19 so that the floss 104 wound on the axle 103 in the cavity 102 of the handle 101 is guided from the axle along the cavity and further the floss passage to the first floss holder 105 which comprises a tensioning means 108 provided with the tensioning means 108 of the tip part 107, said tensioning means being provided with tensioning and guide passages 111 and 113. The floss 104 is applied through the tensioning passage 111 at the base side of the tensioning means, guided further along the floss passage 109 in the outer, or the second, floss holder 110 in the tip part 107, and taken out at the open end 114 of the floss holder. Further, the floss 104 is taken back to the first floss holder 105 and consequently attached to the guide passage 112 at the end of the tensioning means 108.

When the guide passage 112 in the tensioning means is taken to a position parallel to the longitudinal axis of the device by rotating the tip part 107 (FIG. 11), the floss 104 is free to move via the tensioning and guide passages in the tensioning means. The movement of the floss is somewhat, but not entirely, prevented by the transverse position of the tensioning passage (FIG. 10). This allows gripping to the free end of the floss, and also releasing it from the first floss holder after use, and pulling a new unused portion of floss to between the floss holders, and fitting it in a slot or similar element forming the guide passage 112. After this, the floss is tensioned between the floss holders 105, 110 of the device by rotating the tip part 107 away from the device body 100 to its operative position, the tip part advantageously forming a 40° angle with respect to the longitudinal axis of the body. Then, the used floss end may be removed by cutting it, using the cutting means 115 provided in the body of the device.

The device may also be made such that it is ready for use with the tip part parallel to the longitudinal axis of the body.

In a third embodiment of the dental floss holding device according to the invention, the outer floss holder of the device may be arranged to rotate by providing the floss holder end at the body side with a barrel. If this barrel is arranged in connection with the inner floss holder, the outer floss holder may be rotated freely, and the floss may be tensioned and locked with a tensioning means provided in the inner floss holder.

A fourth embodiment of the dental floss holding device is shown by FIGS. 21 and 22. Such a device comprises a first and a second floss holder 201, 202 which may be protected by a cover part 200 and which are essentially parallel to the handle 203, forming between them a fork-like gap 204. In this device, the floss 205 is guided from the cavity in the handle via a tensioning passage 207 within the tensioning part 206 to the floss passage of the first floss holder 201, from which it exits via a hole at the tip of the floss holder. The floss 205 is further fed from a hole in the second floss holder 202 to a floss passage therein, via which it is fed via a guide passage 208 in the tensioning part, exiting the device from the hole located near a cutting element 209.

In the devices according to the invention, the floss 205 is thus attached and tensioned between the floss holders 201 and 202 provided in the device by turning the tensioning means 206 about its longitudinal axis. Consequently, both ends of the floss travelling via the tensioning means are subjected to a tractive power which tightens the floss between the floss holder tips. This ensures that the floss retains its tightness when the device is being used. The floss is at the same time locked securely in place by clamping between the tensioning means outer shell and the surrounding inner wall of the joint passage in the first floss holder. Thus it will not have the chance to loosen to an disadvantageous degree during use, which is most important when using dental floss.

The dental floss holding devices are meant to be build disposable. The axles within them are not intended to be detached or replaced. There is no reason, however, why the devices could not be made to be refilled.

The floss holders and the floss between them may easily be protected by an easy to remove cover part. Such a cover part ensures the hygiene of the device to be maintained also during transport and storing.

It should be understood that the description above and the drawings related thereto are only intended to illustrate the present invention. The invention is therefore not restricted to the embodiment disclosed or determined in the claims, but various kinds of variations and modifications within the scope of the inventive idea set forth the attached claims will be obvious to persons skilled in the art.

What is claimed is:

1. A dental floss holding device comprising:
   a device body;
   a floss passage within the device body;
   an outer floss holder at an end of the device body, a portion of the floss passage being located within the outer floss holder;
   an inner floss holder which is spaced from the outer floss holder and including receiving passages; and
   a tensioning element which is rotatable relative to the device body, the tensioning element including a tensioning passage which is substantially coplanar with a segment of the floss passage, and a guide passage which is substantially coplanar with the receiving passages; wherein when the tensioning element is in a rotational position such that the tensioning passage is aligned with said segment of the floss passage, the guide passage is out of alignment with the receiving passages.

2. The dental floss holding device according to claim 1, wherein the tensioning element includes an elongate element which is rotatable within a joint passage in the inner floss holder.

3. The dental floss holding device according to claim 2, wherein the tensioning element includes a turning arm at one end, the guide passage being located proximate the other end of the tensioning element, with the tensioning passage being located between the guide passage and the turning arm.

4. The dental floss holding device according to claim 2, wherein a transverse cross section of the elongate element includes two body segments, the tensioning passage being located between the body segments, and the body segments each having an arcuate surface which is engageable with a cheek surface within said segment of the floss passage, and each body segment including a flat end surface, the flat end surfaces forming a notch in the elongate element.

5. The dental floss holding device according to claim 2, wherein both the tensioning passage and the guide passage extend through the elongate element, the tensioning passage lying in a plane which is substantially parallel to and spaced from a plane containing the guide passage, and being angularly offset from the guide passage.

6. The dental floss holding device according to claim 5, wherein the tensioning passage and the guide passage are offset by approximately 90 degrees.

7. The dental floss holding device according to claim 2, the dental floss holding device further comprising a floss storage device from which dental floss is passed through the floss passage, the tensioning passage, and the guide passage, wherein the tensioning element is rotatable to a release position, at which position the tensioning passage is substantially perpendicular to the floss passage, and the guide passage is substantially aligned with the receiving passages, which allows dental floss to travel freely through the floss passage, the guide passage, and the tensioning passage.

8. The dental floss holding device according to claim 7, wherein the tensioning element is rotatable into a locked position, at which point a cheek surface within the floss passage engages an exterior surface of the tensioning element, with dental floss held between the cheek surface and the tensioning element.

9. The dental floss holding device according to claim 8, wherein the tensioning element is in the locked position when rotated from about 180 to 270 degrees from the release position.

10. The dental floss holding device according to claim 9, wherein during rotation of the tensioning element from about 0 to 180 degrees from the release position, the tensioning passage does not exert significant tension on the dental floss, so that floss can translate through the tensioning passage.

11. The dental floss holding device according to claim 2, wherein a transverse cross section of the elongate element includes a first and a second body segment, the guide passage being located between the body segments, the first body segment having a surface which is engageable with an interior surface of the joint passage, and a grip notch, the second body segment having a surface which does not engage the interior of the joint passage, and a grip notch.

12. The dental floss holding device according to claim 1, further including an axle carrying dental floss located within a cavity in the device body, the dental floss extending from the axle through the floss passage to a tip of the outer floss holder, then to the receiving passages of the inner floss holder, and then to a cutting device.

13. The dental floss holding device according to claim 1, wherein the dental floss holding device has a longitudinal axis, the tensioning element being an elongate element rotatable about an axis which is substantially perpendicular to the longitudinal axis.

14. The dental floss holding device according to claim 11, wherein the tensioning element and the outer floss holder are rigidly connected, the outer floss holder acting as a turning handle for rotating the tensioning element.

15. A dental floss holding device comprising:
   a handle having a longitudinal axis and a cavity formed therein;
   first and second dental floss holders extending from an end of the handle; and
   an elongated rotatable tensioning element located within an elongated joint within the handle, the tensioning element including a tensioning passage at one end, and a guide passage at its other end, wherein when the tensioning passage is substantially parallel to the longitudinal axis of the handle, the guide passage is substantially perpendicular to the longitudinal axis of the handle.

16. The dental floss holding device according to claim 15, wherein the elongated joint is positioned substantially perpendicularly to the longitudinal axis of the handle, the tensioning element rotating within the joint about an axis which is substantially perpendicular to the longitudinal axis of the handle.

17. The dental floss holding device according to claim 16, further comprising dental floss disposed within the cavity in the handle, and extending from the tensioning passage to the first and second floss holders, and subsequently to the guide passage, wherein when the tensioning element is rotated within the joint, the dental floss is wound around the tensioning element and locked in place.

18. A method for tensioning dental floss, the method comprising:

providing a device including a device body with an internal floss passage, an inner floss holder having receiving passages, and an outer floss holder;

providing a tensioning element including a tensioning passage and a guide passage, the tensioning element being rotatable with respect to the device body;

guiding dental floss through the floss passage, the tensioning passage and the guide passage;

rotating the tensioning element to a release position, at which position the tensioning passage is out of alignment with the floss passage, and the guide passage is substantially aligned with the receiving passages; and rotating the tensioning element through an angular range from the release position to a locking position, at which position the dental floss is substantially prevented from motion within the device body.

19. The method for tensioning dental floss according to claim 18, wherein the step of rotating the tensioning element to a release position includes the step of rotating the tensioning passage until it is about 90 degrees offset from the floss passage.

20. The method for tensioning dental floss according to claim 18, wherein the tensioning passage and the guide passage lie in planes which are substantially parallel to one another and spaced apart, the tensioning passage and the guide passage both extending through the tensioning element, and being oriented substantially perpendicular to one another.

21. The method for tensioning dental floss according to claim 18, wherein the step of rotating the tensioning element to a locking position includes the step of rotating the tensioning element from about 180 to 270 degrees from the release position.

22. The method for tensioning dental floss according to claim 21, wherein during rotation of the tensioning element from about 0 to 180 degrees from the release position, the tensioning passage does not exert significant tension upon the dental floss, allowing the dental floss to translate within the tensioning passage.

23. The method of tensioning dental floss according to claim 21, wherein the step of rotating the tensioning element from the release position to the locking position includes the step of initially releasing a length of floss from the tensioning passage.

24. The method of tensioning dental floss according to claim 20, wherein a cross section of the tensioning element at a plane containing the guide passage includes two body segments each having a notch adjacent to an arcuate surface, the step of rotating the tensioning element from the release position to the locking position including the step of passing the floss over the arcuate surfaces and the notches of the body segments.

25. The method of tensioning dental floss according to claim 24, the step of rotating the tensioning element from the release position to the locking position includes the step of wrapping dental floss around a portion of the tensioning element which is coplanar with the guide passage, thereby exerting tension on the dental floss.

* * * * *